US00PP37259P2

(12) United States Plant Patent
MacGregor et al.

(10) Patent No.: US PP37,259 P2
(45) Date of Patent: Feb. 10, 2026

(54) ***ANEMONE* PLANT NAMED 'MACANE001.2'**

(50) Latin Name: ***Anemone* hybrid**
Varietal Denomination: MACANE001.2

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

(73) Assignee: Elizabeth Macgregor Nursery, Kirkcudbright (GB)

( * ) Notice: Subject to any disclaimer, the term of this patent is extended or adjusted under 35 U.S.C. 154(b) by 0 days.

(21) Appl. No.: 18/831,576

(22) Filed: Apr. 30, 2025

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Samuel R. McCoy, Jr.

(57) ABSTRACT

'MACANE001.2' is a new and distinctive *Anemone* plant which is characterized by a clumping, non-spreading growth habit with a relatively large amount of flowering stems bearing semi-double flowers, flowers born relatively high above the foliage, flowers with tepals arranged in two whorls, tepals with an upper surface that is white and lightly suffused with violet, proximal tepals with a lower surface that is partially or entirely colored violet, and a long flowering season. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Anemone* hybrid.

Variety denomination: The inventive variety of *Anemone* plant disclosed herein has been given the variety denomination 'MACANE001.2'.

BACKGROUND OF THE INVENTION

Parentage: 'MACANE001.2' is the result of a controlled cross-pollination breeding program carried out by the inventors at their commercial nursery in Kirkcudbright, Scotland, in May of 2005. The inventors performed a controlled cross-pollination of an unnamed *Anemone rupicola* (unpatented), the seed parent, with an unnamed *Anemone hybrida* (unpatented), the pollen parent. Seed from said cross was harvested, then germinated, and the resulting seedlings were then grown to a mature size in order to evaluate for desirable commercial characteristics. In August of 2020, the inventors selected the new *Anemone* cultivar due to its unique flower and bloom characteristics. This new and distinctive cultivar was given the name 'MACANE001.2'.

Asexual Reproduction: Asexual reproduction of 'MACANE001.2' was first accomplished in May of 2021 by way of root cuttings at the inventor's nursery in Kirkcudbright, Scotland. After several years of experimentation, 'MACANE001.2' was also asexually reproduced by way of meristematic tissue culture micro propagation at a plant tissue culture laboratory in the Netherlands. Through six cycles of asexual propagation, the variety has shown the unique features of the instant cultivar are stable and reproduce true to type.

SUMMARY OF THE INVENTION

The cultivar 'MACANE001.2' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anemone* cultivar, 'MACANE001.2'. These traits, in combination, distinguish 'MACANE001.2' as a new and distinct cultivar.

1. *Anemone* 'MACANE001.2' exhibits a compact, non-spreading growth habit; and
2. *Anemone* 'MACANE001.2' exhibits a relatively large amount of flowering stems that give rise to dichasial cymes bearing semi-double flowers; and
3. *Anemone* 'MACANE001.2' exhibits flowers with white tepals, some of which are lightly suffused with violet, on the upper surface and violet tepals with white margins on the lower surface; and
4. *Anemone* 'MACANE001.2' exhibits early flowering, from early June to October when grown in Kirkcudbright, Scotland.

BOTANICAL DESCRIPTION OF THE PLANT

Figure 1:
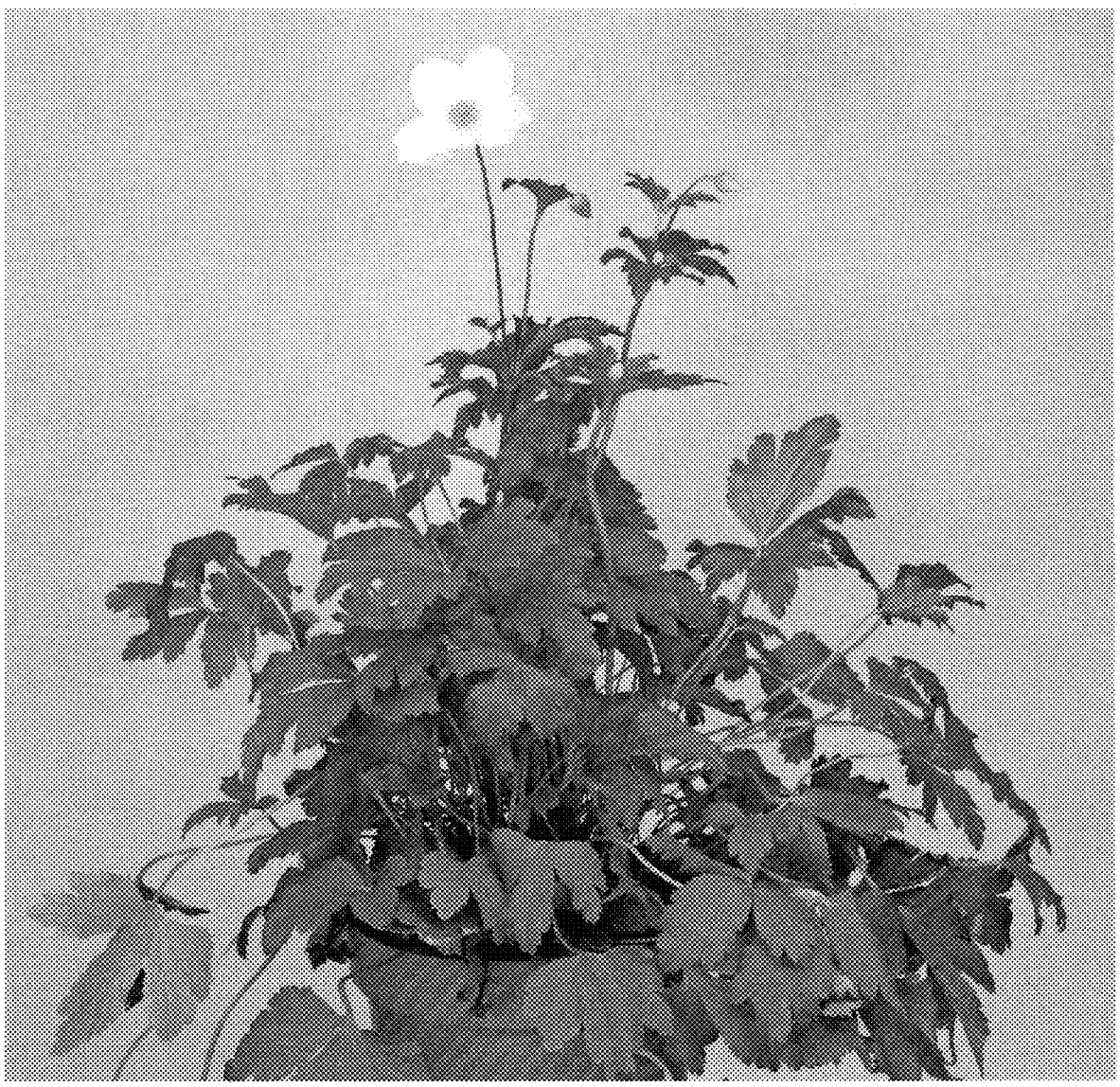
FIG. 1 shows, as nearly true as it is reasonably possible to make the same in color illustrations of this type, the typical foliage and growth characteristics of the new cultivar, 'MACANE001.2'. The plant shown is approximately 8-months-old, potted into a 19 cm nursery pot, grown outdoors in Kirkcudbright, Scotland at a commercial nursery.
Figure 2:
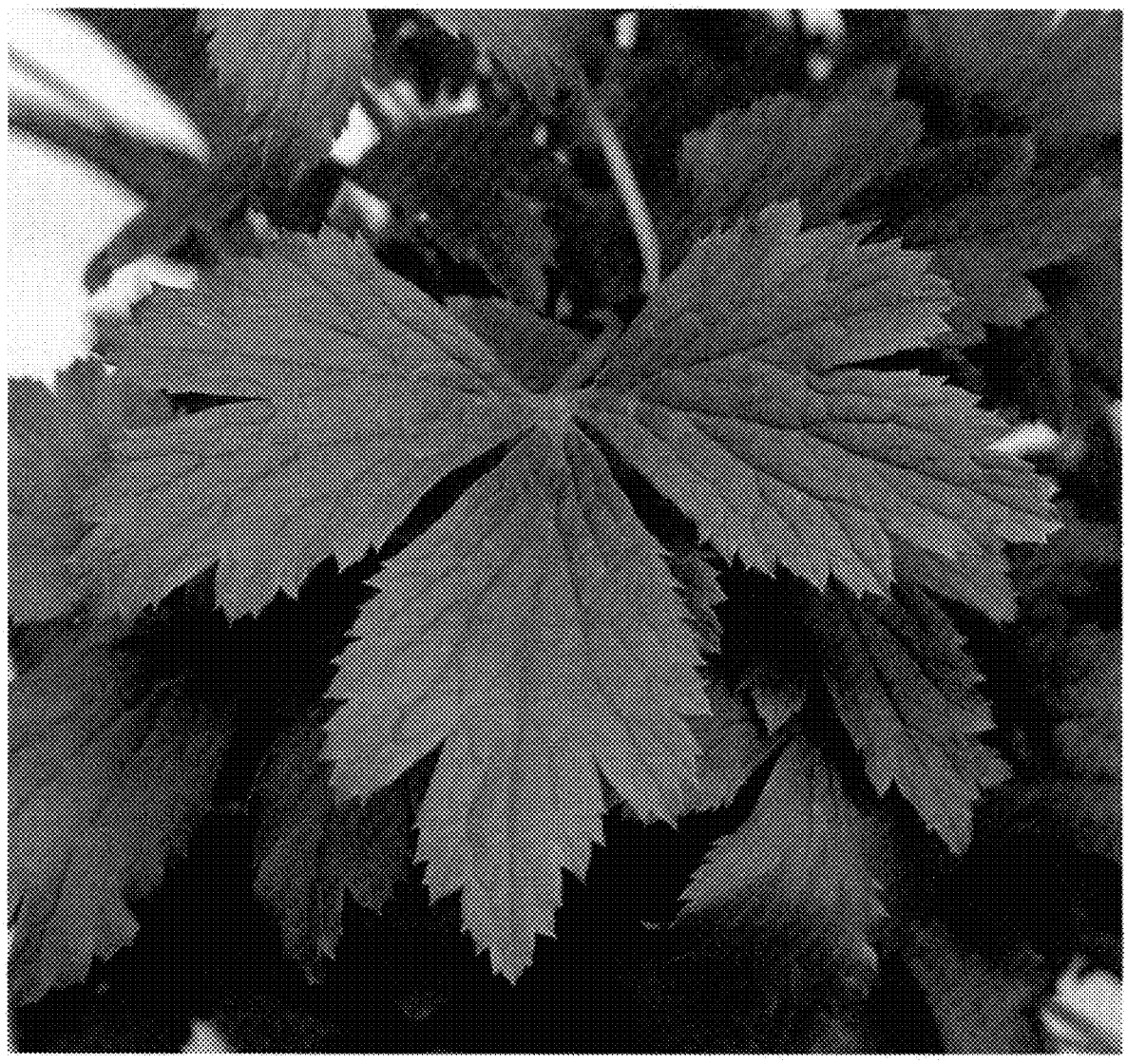
FIG. 2 shows, as nearly true as it is reasonably possible to make the same in color illustrations of this type, the typical foliage of the plant in FIG. 1.
Figure 3:
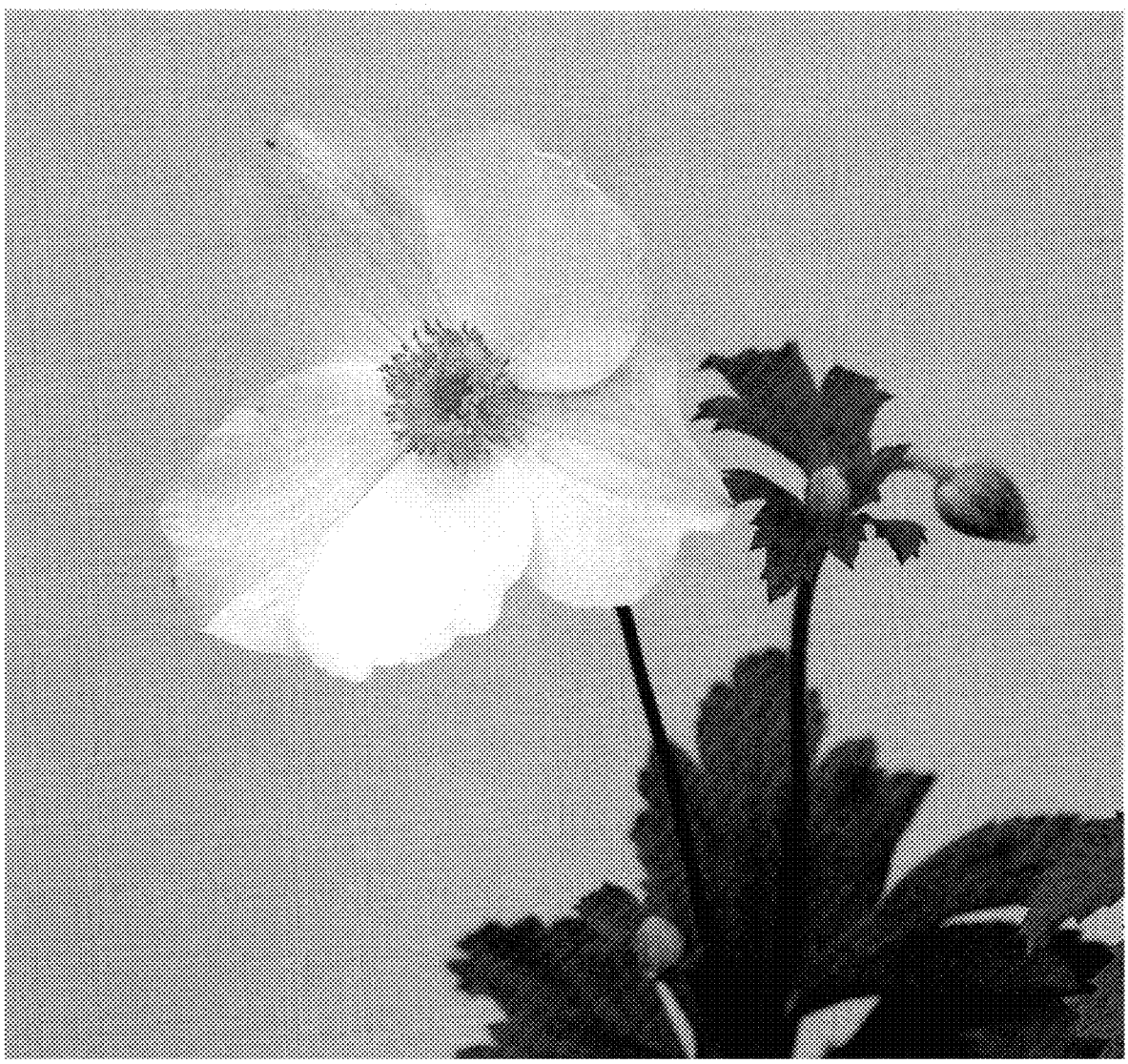
FIG. 3 shows, as nearly true as it is reasonably possible to make the same in color illustrations of this type, the typical flower of the plant in FIG. 1.

The following observations and measurements made in July of 2024 describe an 8-month-old 'MACANE001.2' plant grown in a 19 cm nursery container outdoors at a commercial nursery in Kirkcudbright, Scotland. Plants were grown in full sun to partial shade using accepted fertility and irrigation practices for *Anemone* plants. With the exception of nematicides, no chemical pest control measures were employed. Furthermore, no artificial light or photoperiodic treatments were given to the plants.

Those skilled in the art will appreciate that certain characteristics will vary with older or, conversely, with younger plants. 'MACANE001.2' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'MACANE001.2' and comparisons with the parents and most similar variety of common knowledge are provided below.

General plant description:

*Growth habit*.—Herbaceous perennial; globular plant habit with leaves developing from basal rosettes; flowering stems arising from the rosette also bear foliage; no lateral branching is present.

*Height*.—37.0 cm to the top of the foliar plane; 42.5 to the top of the floral plane.

*Width*.—53.0 cm.

*Propagation*.—Root cuttings and tissue culture. Time to produce flowering plant from rooted cutting — Approximately 6 to 8 weeks. Time to produce a marketable potted plant — Approximately 16 to 20 months.

*Disease and pest resistance*.—'MACANE001.2' exhibits susceptibility in common with the parent including powdery mildew, *Erysiphaceae*, as well as common insect pests such as aphids and spider mites.

*Environmental tolerances*.—Adapt to, at least, USDA Zones 4 to 9 and temperatures ranging from minus 30 degrees Celsius to 35 degrees Celsius; moderate tolerance to rain; moderate tolerance to wind.

Root system:

*Type*.—Moderately fibrous root system.

*Branching*.—Very freely branched.

*Distribution*.—Roots distributed evenly throughout the soil profile, from shallow to deep.

*Density*.—Moderately dense.

*Diameter*.—Largest roots measuring 0.5 mm in diameter.

*Texture*.—Smooth; lacking root hairs.

*Color*.—Greyed-brown, nearest to in between RHS N199C and N199D.

Flowering stem:

*Branching habit*.—Flowering stems arise directly from the basal rosette; stems are basally branched.

*Number of flowering stems per plant*.—4.

*Aspect*.—Terete.

*Length*.—34.5 cm.

*Diameter*.—0.3 cm.

*Internode length*.—23.4 cm.

*Luster*.—Slightly glossy.

*Aspect*.—Average angle of 10 degrees from vertical.

*Strength*.—Strong.

*Pubescence*.—Densely pubescent; hairs are greyed-white, RHS NN156D, and 0.5 mm long, on average.

*Color, mature*.—Yellow-green, nearest to RHS 146C, and strongly suffused with a blend of greyed-orange and grey-brown, RHS 177B and 199B.

*Color at internodes*.—Yellow-green, nearest to RHS 146C, and suffused with greyed-red, nearest to RHS 182B.

Foliage:

*Arrangement*.—Leaves are borne both basally and on the flowering stems.

*Basal leaves*.—Attachment — Petiolate. Arrangement — Alternate. Division — Trifoliate. Compound leaf outline — Broad ovate to near orbicular. Length — 10.3 cm, excluding the petiole. Width — 11.7 cm. Attitude — Upward and outward, at an average angle of 60 degrees to horizontal. Leaflets — Shape — Ovate. Length — 3.4 cm. Width — 5.8 cm. Attitude — Outward, relative to the petiole. Aspect — Slightly convex. Apex — Acute to acuminate. Base — Acute. Margin — Serrulate to incised, moderately to deeply lobed. Sinus orientation — Convergent. Texture, adaxial surface — Sparsely pubescent to near glabrous, and slightly glossy; pubescence is, on average, 1 mm in length. Texture, abaxial surface — Moderately pubescent and slightly glossy. Color — Juvenile color, adaxial surface — Green, nearest to RHS 143A; pubescence color is indistinguishable from surrounding area. Juvenile color, abaxial surface — Yellow-green, nearest to RHS 146B; pubescence colored greyed-white, nearest to RHS 156A. Mature color, adaxial surface — Green, nearest to a blend of RHS 137B and 143A; pubescence color is indistinguishable from surrounding area. Mature color, abaxial surface — Yellow-green to greyed-green, nearest to a blend of RHS 147B and 191A; pubescence colored greyed-white, nearest to RHS 156A. Venation — Type — Laciniate. Vein color, adaxial surface — Yellow-green, nearest to a combination of RHS 144A and 144B. Vein color, abaxial surface — Yellow-green, nearest to a combination of RHS 144A and 144B. Stipules — General — Two leafy stipules present at the base of each leaf. Shape — Oblong to narrow ovate. Length — Average of 3.2 cm. Diameter — Average of 1.4 cm. Texture, adaxial surface — Rugose and pubescent, strigose hairs have an average length of 1.0 mm, sparsely present and colored white, nearest to RHS NN155B. Texture, abaxial surface — Rugose and pubescent, strigose hairs have an average length of 1.0 mm, sparsely present and colored greyed-white, nearest to RHS 156A. Color of the adaxial and abaxial surfaces — Greyed-white, nearest to RHS 157C and fading yellow-green, nearest to RHS 147D, towards the distal end. Petiole — Length — 22.5 cm. Diameter — 0.2 cm. Strength — Strong. Texture, adaxial and abaxial surfaces — Sparsely pubescent, average length of hairs is 0.15 cm. Luster, adaxial and abaxial surfaces — Slightly to moderately glossy. Color, adaxial surface — Yellow-green, nearest to RHS 144A, fading to purple, nearest to RHS N77B, proximally; pubescence color is indistinguishable from surrounding area. Color, abaxial surface — Yellow-green, nearest to RHS 144A, fading to red-purple, nearest to RHS 64A; pubescence color is indistinguishable from surrounding area.

*Cauline leaves*.—Attachment — Petiolate. Attitude — Upward and outward, at an average angle of 45 degrees to horizontal. Arrangement — Opposite. Division — Simple. Shape — Trilobate; lobes are deeply lobed to near-cleft. Lobes — Depth of sinuses — Varying from deep to very deep. Sinus orientation — Convergent. Length — 7.0 cm. Width — 7.4 cm. Attitude — Outward, relative to the petiole. Aspect — Slightly convex. Apex — Acute. Base — Attenuate. Margin — Serrulate to incised, moderately to deeply lobed. Texture, adaxial surface — Sparsely pubescent to near glabrous, and slightly glossy; pubescence is, on average, 1 mm in length. Texture, abaxial surface — Moderately pubescent and slightly glossy. Color — Juvenile color, adaxial surface — Green, nearest to RHS 143A; pubescence color is indistinguishable from surrounding area. Juvenile color, abaxial surface — Yellow-green, nearest to RHS 146B; pubescence colored greyed-white, nearest to RHS 156A. Mature color, adaxial surface — Green, nearest to a blend of RHS 137B and 143A; pubescence color is indistinguishable from surrounding area. Mature color, abaxial surface — Yellow-green to greyed-green, nearest to a blend of RHS 147B and 191A; pubescence colored greyed-white, nearest to RHS 156A. Venation — Type — Laciniate. Vein color, adaxial surface — Yellow-green, nearest to a combination of RHS 144A and 144B. Vein color, abaxial surface — Yellow-green, nearest to a combination of RHS 144A and 144B. Stipules — General — Two leafy stipules present at the base of each leaf. Shape — Oblong to narrow ovate. Length — Average of 0.6 cm. Diameter — Average of 0.9 cm. Texture, adaxial surface — Rugose and pubescent, strigose hairs have an average length of 1.0 mm, sparsely present and colored white, nearest to RHS NN155B. Texture, abaxial surface — Rugose and pubescent, strigose hairs have an average length of 1.0 mm, sparsely present and colored greyed-white, nearest to RHS 156A. Color, adaxial and abaxial surface — Yellow-green, nearest to RHS 146D. Petiole — Length — 0.4 cm. Diameter — 0.6 cm. Strength — Strong. Texture, adaxial and abaxial surfaces — Moderately covered with soft hairs; average length of hairs is 0.15 cm; pubescence indistinguishable from surrounding area. Luster, adaxial and abaxial surfaces — Very glossy. Color, adaxial surface — Green, nearest to a combination of RHS 143B and 143C. Color, abaxial surface — Yellow-green, nearest to RHS 144B.

Inflorescence:

*Habit*.—Dichasial cyme arising directly from the terminal of the flowering stems.

*Natural flowering season*.—Early June to October in Kirkcudbright, Scotland.

*Time to flower or response time*.—Approximately 10 months.

*Height*.—16.5 cm.

*Diameter*.—11.5 cm.

*Quantity of flowers per inflorescence*.—3, on average.

*Quantity of flowers and flower buds per plant*.—15, on average.

*Peduncles*.—Inflorescence is a sessile cyme; no peduncles are present.

Bud:

*Shape*.—Ovate.

*Length*.—Average of 1.4 cm.

*Diameter*.—Average of 0.8 cm.

*Texture*.—Tomentose; hairs with an average length of 0.1 cm and colored greyed-green, nearest to RHS 198D.

*Luster*.—Matte.

*Color*.—Greyed-green, nearest 195A.

Flower:

*Type and form*.—Rotate flowers with undifferentiated sepals and petals arranged in two whorls with 3 lower tepals and 2 upper lateral tepals.

*Attitude*.—Upright to slightly outward; slightly pendulous at dusk.

*Flowering habit*.—Freely flowering.

*Flower longevity on plant*.—Approximately 10 days.

*Persistent or self-cleaning*.—Self-cleaning

*Fragrance*.—Non-fragrant.

*Depth*.—Average of 2.0 cm.

*Diameter*.—Average of 6.7 cm.

*Tepals*.—Quantity — 5 per flower. Arrangement — Rotate; the unfused tepals arranged in 2 whorls. Length — 3.9 cm. Width — 2.9 cm. Shape — Obovate to broad elliptic. Apex — Obtuse to emarginate. Base — Cuneate. Margin — Entire; slightly undulated. Texture, luster and pubescence of the upper surface — Matte and moderately velvety. Texture, luster and pubescence of the lower surface — Matte and densely covered with appressed soft, silky hairs; average length of hairs is 0.1 cm; colored white, nearest to RHS NN155D. Color — When opening, upper surface — White, nearest to RHS NN155D, and fading to yellow-green towards the base, nearest to RHS 154D; central zone is lightly suffused with violet, nearest to RHS 85A. When opening, lower surface — Upper tepals are white, nearest to RHS NN155D. Lower tepals are partially or entirely colored violet, nearest to RHS 85A, and broadly margined white, nearest to RHS NN155D. Fully opened, upper surface — White, nearest to RHS NN155D, and fading to yellow-green towards the base, nearest to RHS 154D; central zone of the lower tepals is lightly suffused with violet, nearest to RHS 85A. Fully opened, lower surface — Upper tepals are white nearest to RHS NN155D. Lower tepals are violet, nearest to RHS 85A, and broadly margined white, RHS NN155D. Tepal venation —

Fully opened, upper surface — No venation is visible on the upper tepals with the exception of the basal portion where veins are green-white, nearest to RHS 157D. The lower tepals are violet, RHS 86B, in the areas that are suffused with violet; veins are not visible in the white portions of the lower tepals. Fully opened, lower surface — No venation is visible on the upper tepals. The lower tepal veins are violet, nearest to in between 86B and 86C, in the violet portion of the tepal and are not visible in the white portions of the margins.

*Pedicels*.—Length — Average of 10.3 cm. Diameter — Average of 0.175 cm. Angle — Average angle to soil level is approximately 10 degrees. Strength — Strong. Texture and pubescence — Moderately covered with soft hairs; average length of hairs is 1.0 mm; hairs colored greyed-white, nearest to RHS 156D. Luster — Slightly glossy. Color — Yellow-green, nearest to RHS 146A, and heavily suffused with brown, nearest to RHS 200B, with the exception of the distalmost portion of the pedicel.

Reproductive organs:

*Stamens*.—Quantity — Approximately 200. Anthers — Shape — Oblong. Length — Approximately 1.5 mm. Width — Approximately 0.1 cm. Color — Yellow, nearest to RHS 13A. Filaments — Length — 0.6 cm, on average. Color — Green-yellow, nearest to RHS 1C.

*Pollen*.—Color — Yellow, RHS 11D. Quantity — None to sparse.

*Pistil*.—Quantity — 200, on average. Length — 1.2 mm. Style — Length — 1.0 mm. Color — Green, RHS 143B. Stigma — Shape — Club-shaped. Dimensions — 0.2 mm long and 0.2 mm in diameter. Color — Yellow-green, nearest to RHS 152A.

*Ovary color*.—Yellow-green, RHS 145D.

Seed and fruit: Fruit and seeds have not been observed.

COMPARISONS WITH THE PARENT PLANTS

Plants of the new cultivar 'MACANE001.2' may be distinguished from its seed parent, an unnamed *Anemone rupicola* (unpatented), by the characteristics described in Table 1.

TABLE 1

Comparison Between 'MACANE001.2 and The Seed Parent.

| Characteristic | 'MACANE001.2' | The Seed Parent |
|---|---|---|
| Growth rate. | Faster growing than the seed parent. | Slower growing than 'MACANE001.2'. |
| Size. | Larger than the seed parent, approximately 42.5 cm tall. | Smaller than 'MACANE001.2', approximately 25 cm tall. |
| Flowering season. | Longer than the seed parent. | Shorter than 'MACANE001.2'. |

Plants of the new cultivar 'MACANE001.2' differ from the pollen parent, an unnamed *Anemone* plant (unpatented), by the characteristics described in Table 2.

TABLE 2

Comparison Between 'MACANE001.2' and The Pollen Parent

| Characteristic | 'MACANE001.2' | The Pollen Parent |
|---|---|---|
| Growth habit. | Clumping. | Spreads vigorously. |
| Size. | Smaller than the pollen parent, approximately 42.5 tall. | Larger than 'MACANE001.2', approximately 100 cm tall. |
| General coloration of the upper surface of the perianth when fully opened. | Upper lateral tepals are white, while the lower whorl of tepals are white and lightly suffused with violet. | Upper lateral tepals are white, while the lower whorl of tepals are white and lightly suffused with dark pink. |
| General coloration of the lower surface of the perianth when fully opened. | Upper lateral tepals are white, while the lower whorl of tepals are violet and broadly margined white. | Upper lateral tepals are white, while the lower whorl of tepals are white and strongly suffused with dark pink. |

COMPARISONS WITH THE MOST SIMILAR VARIETY OF COMMON KNOWLEDGE

Plants of the new cultivar 'MACANE001.2' are most similar to the commercial variety, *Anemone* 'MACANE001' (U.S. Plant Pat. No. 23,132). A comparison of 'MACANE001.2' with 'MACANE001' is described in Table 3.

TABLE 3

Comparison Between 'MACANE001.2' and 'MACANE001'

| Characteristic | 'MACANE001.2' | 'MACANE001' |
|---|---|---|
| Plant height to the top of the floral plane. | Shorter than 'MACANE001'. | Taller than 'MACANE001.2'. |
| General coloration of the upper surface of the perianth when fully opened. | Upper lateral tepals are white, while the lower whorl of tepals are white and lightly suffused with violet. | All tepals are white. |
| General coloration of the lower surface of the perianth when fully opened. | Upper lateral tepals are white, while the lower whorl of tepals are violet and broadly margined white. | Upper lateral tepals are white and lightly streaked with violet, while the lower whorl of tepals are violet-blue, streaked with violet, narrowly to and broadly margined white. |
| Stem color. | Darker, than 'MACANE001', closer to brown. | Lighter purple than 'MACANE001.2'. |

That which is claimed is:

1. A new and distinct variety of *Anemone* plant named 'MACANE001.2', substantially as described and illustrated herein.

* * * * *